United States Patent [19]

Dombou et al.

[11] Patent Number: 4,886,749
[45] Date of Patent: Dec. 12, 1989

[54] PROCESS FOR PRODUCING DIADENOSINE TETRAPHOSPHATE AND DERIVATIVES THEREOF

[75] Inventors: Munehiko Dombou; Isao Tomioka; Senji Kitabatake; Hiroshi Nakejima, all of Kyoto, Japan

[73] Assignee: Unitika Ltd., Amagasaki, Japan

[21] Appl. No.: 54,975

[22] Filed: May 28, 1987

[30] Foreign Application Priority Data

May 28, 1986 [JP] Japan .................. 61-122723

[51] Int. Cl.$^4$ .................. C12P 19/36; C12N 9/12; C12R 1/01; C12R 1/07
[52] U.S. Cl. .................. 435/89; 435/90; 435/194; 435/822; 435/832
[58] Field of Search .................. 435/88, 89, 90, 91, 435/92, 194, 832, 822

[56] References Cited

U.S. PATENT DOCUMENTS

| | | | |
|---|---|---|---|
| 4,331,762 | 5/1982 | Nakajima et al. | 435/194 |
| 4,349,631 | 9/1982 | Kagayama et al. | 435/194 |
| 4,572,894 | 2/1986 | Imahori et al. | 435/68 |
| 4,584,272 | 4/1986 | Imahori et al. | 435/194 |

FOREIGN PATENT DOCUMENTS

| | | | |
|---|---|---|---|
| 1173768 | 9/1984 | Canada | 435/194 |
| 0050007 | 5/1982 | European Pat. Off. | 435/194 |
| 0025088 | 2/1977 | Japan | 435/194 |
| 53-11589 | 1/1978 | Japan . | |
| 6099792 | 8/1981 | Japan | 435/194 |
| 6154992 | 11/1981 | Japan | 435/194 |
| 3049079 | 3/1988 | Japan | 435/194 |

OTHER PUBLICATIONS

Goerlich et al., Eur. J. Biochem. 126:135–142 (1982).
Eur. Patent Application No. 0084975-Imahori et al. 3-08-83.
Barker, Eur. J. Biochem. 125:357–360 (1982).

*Primary Examiner*—Ronald W. Griffin
*Assistant Examiner*—Stephanie W. Zitomer
*Attorney, Agent, or Firm*—Sughrue, Mion, Zinn, Macpeak, and Seas

[57] ABSTRACT

A process for producing diadenosine tetraphosphate or derivatives thereof in very high yields with little formation of undesired by-products is disclosed. The process comprises reacting adenosine-5'-triphosphate or a derivative thereof with an amino acid under the catalytic action of an aminoacyl-tRNA synthetase in the presence of an enzyme that converts adenosine-5'-diphosphate to adenosine-5'-triphosphate. The formation of by-products can be substantially completely inhibited if the last-mentioned enzyme is used in combination with an enzyme that converts adenosine-5'-monophosphate to adenosine-5'-diphosphate.

10 Claims, No Drawings

PROCESS FOR PRODUCING DIADENOSINE TETRAPHOSPHATE AND DERIVATIVES THEREOF

FIELD OF THE INVENTION

The present invention relates to a process for producing diadenosine tetraphosphate and derivatives thereof which are useful as medicines or starting materials for their production.

BACKGROUND OF THE INVENTION

Diadenosine tetraphosphate and derivatives thereof have various physiological activities, such as stimulation of DNA synthesis in $G_1$-arrested baby hamster kidney (BHK) cells (F. Grummt, *Proc. Natl; Acad. Sci. USA*, Vol. 75, p.371 (1978)), inhibition of phosphorylation of immunoglobulin G (P.F. Maness et al., *J. Biol. Chem.*, Vol.258 p.4055 (1983)), and inhibition of blood-platelet aggregation by adenosine diphosphate (M.J. Harrison et al., *FEBS Letters*, Vol.54, p.57 (1975)). Because of these activities, diadenosine tetraphosphates and derivatives thereof has been developed as being a substance which is hoped to be suitable for use as medicines such as an antithrombogenic agent, a thrombus preventing agent, etc., and starting materials for their production.

Methods for preparing diadenosine tetraphosphate (hereinafter collectively referred to as $A_{p4}A$) and derivatives thereof have been reported by O. Goerlich et al in *Eur. J. Biochem.*, Vol.126, p.135 (1982): in the presence of various aminoacyl-tRNA synthetases such as *E. coli* lysyl-tRNA synthetase, histidyl-tRNA synthetase, phenylalanyl-tRNA synthetase, yeast lysyl-tRNA synthetase, phenylalanyl-tRNA synthetase, *Fusarium* phenylalanyl-tRNA synthetase, and phenylalanyl-tRNA synthetase from sheep liver cells, diadenosine tetraphosphate can be synthesized from adenosine-5'-triphosphate (hereinafter referred to as ATP), and dideoxyadenosine tetraphosphate, which is a derivative of diadenosine tetraphosphate can be synthesized from an ATP derivative, 2'-deoxyadenosine-5'-triphosphate.

The major disadvantage of this method which consists of reacting ATP or derivatives thereof (hereinafter referred to as NTP) with amino acids in the presence of aminoacyl-tRNA synthetases is that in addition to the desired $A_{p4}A$ or derivatives thereof, diadenosine triphosphate (hereinafter referred to as $A_{p3}A$) or derivatives thereof, adenosine-5'-diphosphate (ADP) or derivatives thereof (hereinafter referred to as NDP), and adenosine-5'-monophosphate (AMP) or derivatives thereof (hereinafter referred to as NMP) are formed as by-products. Formation of such by-products results in an uneconomical use of the expensive starting material NTP and leads to a lower yield of $A_{p4}A$ or derivatives thereof. Furthermore, it is extremely difficult to separate the desired $A_{p4}A$ or derivatives thereof from the reaction product if it contains $A_{p3}A$ or derivatives thereof.

Japanese Patent Application (OPI) No. 146539/1983 (corresponding to U.S. Pat. No. 4,572,894) (the term "OPI" as used herein means an unexamined published Japanese patent application) describes use of an aminoacyl-tRNA synthetase as a condensing agent in synthesizing peptide or peptide derivatives from amino acids. Japanese Patent Application (OPI) No. 106296/1984 (corresponding to U.S. Ser. No. 461,308 filed on Jan. 26, 1983 and European Patent No. 84975) describes use of one enzyme for converting AMP to ADP and one enzyme for converting ADP to ATP in combination for producing ATP from AMP, the resulting ATP then being used to synthesize a physiologically active substance. These descriptions, however, are not directed to the synthesis of diadenosine tetraphosphate or derivatives thereof.

SUMMARY OF THE INVENTION

An object, therefore, of the present invention is to provide a process by which $A_{p4}A$ or derivatives thereof can be produced in a very high yield without forming $A_{p3}A$ or derivatives thereof, or NDP as a by-product.

The present inventors conducted intensive studies in order to attain this object and have now found that $A_{p4}A$ or derivatives thereof can be produced in an extremely high yield without forming $A_{p3}A$ or derivatives thereof, or NDP as a by-product when the reaction was carried out in the presence of an enzyme capable of converting ADP to ATP. The present invention has been accomplished on the basis of this finding.

Thus, the present invention is directed to a process for producing diadenosine tetraphosphate or a derivative thereof by reacting adenosine-5'-triphosphate or derivatives thereof with an amino acid under the catalytic action of an aminoacyl-tRNA synthetase, wherein said reaction is carried out in the presence of an enzyme that converts adenosine-5'-diphosphate to adenosine-5'-triphosphate.

According to the present invention, $A_{p4}A$ or derivatives thereof can be produced in a very high yield without forming $A_{p3}A$ or derivatives thereof, NDP, or NMP as a by-product.

DETAILED DESCRIPTION OF PREFERRED EMBODIMENTS

The most important feature of the present invention is that the reaction between NTP and amino acids that is catalyzed by an aminoacyl-tRNA synthetase is carried out in the presence of an enzyme for converting ADP to ATP. It is particularly preferable that the reaction is performed in two stages, one being conducted in the presence of an enzyme for converting AMP to ADP, while the other is carried out in the presence of an enzyme for converting ADP to ATP. In this preferred case, no NMP will be formed as a by-product in the second stage of reaction, which therefore does not require any step of separating NMP from the reaction product.

Adenylate kinase may be used in the present invention as an enzyme for converting AMP to ADP. In this case, NTP is used as a phosphate donor to NMP. Many enzymes can be used for the purpose of converting ADP to ATP, including acetate kinase, carbamate kinase, creatine kinase, 3-phosphoglycerate kinase, pyruvate kinase and polyphosphate kinase. In consideration o the ease of availability, acetate kinase is most advantageously used. In this case, acetyl phosphate is used as a phosphate donor. Acetyl phosphate may be used in salt forms such as ammonium, potassium-lithium and sodium salts, and, in consideration of the ease of availability, disodium salts are preferably used. If adenylate kinase and acetate kinase are used, NTP and acetyl phosphate are used as phosphate donors to the respective enzymes. However, NTP as the final product of conversion can be recycled for use as a phosphate donor, so the only phosphate donor that has to be added to the reaction system is acetyl phosphate.

Any of the aminoacyl-tRNA synthetases that have the ability to synthesize $A_p4A$ or derivatives thereof may be used in the present invention. Specific examples of usable aminoacyl-tRNA synthetases include: *E. coli* lysyl-tRNA synthetase, histidyl-tRNA synthetase, phenylalanyl-tRNA synthetase; yeast lysyl-tRNA synthetase, phenyl-alanyl-tRNA synthetase; Fusarium phenylalanyl-tRNA synthetase, leucyl-tRNA synthetases from heat-resistant bacteria such as *Bacillus stearothermophilus*, and phenylalanyl-tRNA synthetase from sheep liver cells. Usable amino acids are u-amino acids such as: tyrosine, alanine, leucine, isoleucine, phenylalanine, methionine, lysine, serine, valine, asparagine, aspartic acid, glycine, glutamine, glutamic acid, cysteine, threonine, tryptophan, histidine, proline and arginine. These amino acids may be either in an L- or D-form.

The choice of aminoacyl-tRNA synthetase to be used should be made in consideration of its specificity for the amino acid with which it is used; for instance, leucyl-tRNA synthetase is used as a leucine-specific aminoacyl-tRNA synthetase.

The enzymes mentioned above are desirably produced by microorganisms that have optimum growth temperatures within the range of 50° to 85° C. and which are exemplified by the following: microorganisms of the genus *Bacillus* such as *Bacillus stearothermophilus, Bacillus brevis, Bacillus coagulans, Bacillus thermoproteolytics* and *Bacillus acidocaldarius;* microorganisms of the genus *Clostridium;* microorganisms of the genus *Thermoactinomyces;* microorganisms of the genus *Achromobacter;* microorganisms of the genus *Streptomyces;* microorganisms of the genus *Micropolyspora;* microorganisms of the genus *Thermus* such as *Thermus aquaticus, Thermus thermophilus* and *Thermus flavus;* microorganims of the genus *Thermomicrobium;* and microorganisms of the genus *Cardelia.* Mesophiles (optimum growth temperature is 20 to 45° C.) into which the gene of one of the microorganisms listed above has been incorporated may also be used as sources from which the aminoacyl-tRNA synthetases used in the present invention can be produced. Cloning of aminoacyl-tRNA synthetase gene is achieved by general methods. For example, *Bacillus stearothermophilus* chromosomal DNA is partially digested with restriction endonuclease. The resulting digest is ligated with a plasmid vector, and then, *Escherichia coli* is transformed by the recombinant DNA plasmid. The clone having aminoacyl-tRNA synthetase activity at high temperature (>50°) is selected and the clone is used as the source of aminoacyl-tRNA synthetase (*Eur, J. Biochem.*, Vol.125, pp.357–360 (1982)). Among the microorganisms mentioned above, *Bacillus stearothermophilus* is particularly suitable for the production of adenylate kinase and acetate kinase.

The term "derivatives of diadenosine tetraphosphate" as used herein means those compounds which have diadenosine tetraphosphate in their skeletal structure and which can be produced by conversion of their constituents (i.e., derivatives of adenosine triphosphate) as catalyzed by aminoacyl-tRNA synthetases.

Examples of such derivatives of diadenosine tetraphosphate include those which are the $N^6$-alkylation, carboxyalkylation, benzoylation and carboxybenzoylation derivatives of the adenine ring, halogenated, hydroxy and deamino derivatives of the adenine ring, and 2'-deoxy, 3'-deoxy, 2',3'-dideoxy, deoxyamino and deoxyhalo derivatives of ribose. More specifically, the typical examples include $N^6$, $N^6$-dicarboxymethyl adenosine tetraphosphate, $N^6$, $N^6$-dicarboxy-ethyl adenosine tetraphosphate, $N^6$, $N^6$-(P-dicarboxybenzoyl) adenosine tetraphosphate, di-8-bromoadenosine tetraphosphate, as well as 2'-deoxy, 3'-decyoxy and 2',3'-dideoxy derivatives of these compounds.

Production of $A_p4A$ or derivatives thereof in accordance with the present invention may be achieved by charging into the same reactor NTP, amino acid, an aminoacyl-tRNA synthetase, and an enzyme for converting ADP to ATP, and then allowing NTP to react with the amino acid in said reactor. Any reactor may be employed, so long as it will permit the intended reaction to proceed smoothly, and the choice of its size and shape may be made on the basis of such factors as the amounts of enzymes used, the conbentration of substrate solution, its pH and supply rate, and the reaction temperature employed.

Membrane or column reactors may typically be used in the practice of the present invention. Membrane reactors are particularly effective since the reaction product attained is of a low molecular weight. On the other hand, enzymes are high-molecular weight substances and can be confined within the reactor throughout cyclic performance of the reaction. If a column reactor is used, it may be packed with the necessary enzymes after they have been immobilized by being bound to, entrapped in or adsorbed on suitable carriers such as, for example, derivatives of polysaccharides (e.g. cellulose, dextran and agarose), derivatives of vinyl polymers (e.g. polystyrene, ethylene-maleic acid copolymer and cross-linked polyacrylamide), derivatives of polyamino acids or amides (e.g. L-alanine/L-glutamic acid copolymer and polyaspartic acid), or derivatives of inorganic materials (e.g. glass, alumina and hydroxyapatite).

The foregoing description of the reactors that can be used in the present invention assumes that reaction is carried out continuously. Other types of reactor can be employed to attain the same purpose. If desired, reaction may be performed batchwise in a reactor of a batch system.

If $A_p4A$ or derivatives thereof is produced in a reactor of batch system, the following reaction conditions are typically used: NTP is desirably added in an amount of at least 10 μM, preferably at least 1 mM, with 10 mM or more being particularly preferable; an amino acid is desirably added in an amount of at least 1 pM, preferably at least 10 μM, with 0.1 mM or more being particularly preferable; acetyl phosphate is desirably added in an amount corresponding to from 10 to $1/10^2$ equivalents, preferably from 2 to 1/10 equivalents, with respect to the concentration of NTP, with from 1 to ½ equivalents being particularly preferable. These starting materials may be added by any suitable method; all of them may be added at a time before starting the reaction, or they may be added in divided portions as reaction proceeds. With a view to allowing the reaction to proceed smoothly, pyrophosphatase, or metal ions such as magnesium, manganese, calcium, cobalt and cadmium ions may be added. The pH of the reaction system varies with the specific type of enzymes used, but values relatively near neutrality (e.g., from 5 to 11, and preferably from 6 to 8) may be employed, with buffer solutions being desirably used to achieve pH adjustment. Ordinary buffer solutions that are adapted for the purpose of attaining these pH values can be employed.

Reaction temperatures can be selected from any range in which reaction will proceed smoothly without experiencing any enzyme inactivation, and a preferable range is from 20° to 50° C.

The reaction product obtained by the process of the present invention contains no $A_{p3}A$ or derivatives thereof and can be subjected to ion-exchange chromatography, affinity chromatography, gel filtration chromatography, or other known techniques of purification to easily isolate he desired $A_{p4}A$ or derivatives thereof.

The following examples are provided for the purpose of further illustrating the present invention but are in no way to be considered as limiting.

REFERENCE EXAMPLE 1

Six kilograms of *Bacillus stearothermophilus* UK 788 cells (FERM P-5141 (FERM BP-2373) FERM: Fermentation research institute, Agency of Industrial Science and Technology, Ministry of International Trade and Industry in Japan) were suspended in two volumes of 100 mM tris-HCl buffer solution (pH, 7.5). The suspended cells were disrupted with a Dyno mill and the insoluble matter was removed by centrifugation to obtain a crude extract containing a leucine-specific leucyl-tRNA synthetase. The crude extract was passed through a column packed with Matrex Gel Blue A (manufactured by Amicon) that had been equilibrated with a 50 mM tris buffer solution (pH, 7.5) containing 5 mM mercaptoethanol, 2 mM ethylenediaminetetraacetic acid sodium salt, and 0.1 mM phosphophenyl sulfonyl fluoride. The column was eluted with the same buffer containing potassium chloride at a linear speed of 60 cm.hr$^{-1}$ so as to obtain fractions containing leucyl-tRNA synthetase. The fractions were combined, concentrated and desalted to recover a crude enzyme solution containing the leucinespecific leucyl-tRNA synthetase (yield: ca. 70%). All of the steps described were carried out at 4° C.

REFERENCE EXAMPLE 2

Five kilograms of *E. coli* K 12 cells were suspended in two volumes of 100 mM tris-HCl buffer solution (pH, 7.5). The suspended cells were disrupted with a Dayno mill and the insoluble matter was removed by centrifugation to obtain a crude extract containing a lysine-specific lysyl-tRNA synthetase. The crude extract was passed through a column packed with Matrex Gel Blue A (manufactured by Amicon) that had been equilibrated with a 50 mM tris buffer solution (pH, 7.5) containing 5 mM mercaptoethanol and 2 mM ethylenediaminetetraacetic acid sodium salt. The column was eluted with the same buffer containing potassium chloride at a linear speed of 60 cm.hr$^{-1}$ so as to Obtain fractions containing lysyl-tRNA synthetase. The fractions were combined, concentrated and desalted to recover a crude enzyme solution containing the lysine-specific lysyl-tRNA synthetase (yield: ca. 65%). All of the steps described above were carried out at 4° C.

EXAMPLE 1

Using the leucyl-tRNA synthetase prepared in Reference Example 1, as well as *Bacillus stearothermophilus* acetate kinase and adenylate kinase (commercially available from Seikagaku Kogyo Co., Ltd.), synthesis of $A_{p4}A$ was conducted by a batch method in the following manner: a reaction solution was first prepared by mixing 12.7 mM ATP, 10 mM leucine, 20 mM magnesium chloride hexahydrate, 2 units/ml pyrophosphatase (manufactured by Böehringer Mannheim), 30 units/ml acetate kinase, 46 units/ml adenylate kinase, 0.25 units/ml leucyl-tRNA synthetase and 100 mM Hepes buffer solution (pH, 7.5); reaction was started by adding 14 mmol/l of acetyl phosphate to the resulting reaction solution and continued at 40° C. for 2 hours; thereafter, 4.6 mmol/l of acetyl phosphate was further added and the reaction was continued for an additional 2 hours; another 4.6 mmol/l of acetyl phosphate was added and the reaction was continued further for 5 more hours.

The resulting reaction product was analyzed by high-performance liquid chromatography on a Novapak $C_{18}$ (manufactured by Waters); $A_{p4}A$ had formed in an amount of 5.1 mM (yield: ca. 80%) but no $A_{p3}A$, AMP, or ADP was detected.

A portion (200 ml) of this reaction solution was applied to a DEAE Sepharose Fast Flow type column (manufactured by Pharmacia Fine Chemicals) equilibrated with 100 mM triethylammonium bicarbonate buffer (pH, 7.6) and subjected to gradient elution with 150 to 350 mM of triethylammonium bicarbonate buffer (pH, 7.6). The $A_{p4}A$ fractions were combined to attain 530 mg of $A_{p4}A$. This purified product was verified as $A_{p4}A$ by determination of its proton and phosphorus NMR spectra.

COMPARATIVE EXAMPLE 1

Reaction was carried out as in Example 1 except that no acetate kinase, adenylate kinase, or acetyl phosphate was added.

Analysis of the reaction product by high-performance liquid chromatography in a Novapak $C_{18}$ (manufactured by Waters) using a solvent of acetonitrile/water (20/80) and 5 mM tetra-n-butylammonium bromide at flow rate of 3 ml/min showed that in addition to 3.1 mM (yield: ca. 49%) of $A_{p4}A$, 2.3 mM AMP, 0.6 mM ADP and 2 mM $A_{p3}A$ had formed as by-products.

EXAMPLE 2

*Bacillus stearothermophilus* acetate kinase and adenylate kinase (commercially available from Seikagaku Kogyo Co., Ltd.), as well as the leucyl-tRNA synthetase prepared in -Reference Example 1 and pyrophosphatase (manufactured by Böehringer Mannheim) were individually immobilized on CN-Br-activated Sepharose 4B (manufactured by Pharmacia Fine Chemicals). The thus immobilized enzymes (acetate kinase, 300 units; adenylate kinase, 400 units; leucyl-tRNA synthetase, 3 units; pyrophosphatase, 20 units) were packed into a single column (capacity: 5 ml).

A starting material was prepared by dissolving 10 mM ATP, 5 mM acetyl phosphate and 10 mM leucine in 100 mM Hepes buffer (pH, 7.0) containing 10 mM magnesium chloride. This starting material was fed into the immobilized enzyme-packed column from the top at a flow rate of 1 ml/hr, with the reaction product being continuously withdrawn from the bottom of the column.

The resulting reaction product was analyzed by the same method as used in Example 1; 4.8 mM (yield: ca. 96%) of $A_{p4}A$ had formed but no $A_{p3}A$, AMP, or ADP was detected. Consistent production of $A_{p4}A$ lasted for the next 24 hours.

COMPARATIVE EXAMPLE 2

Reaction was carried out as in Example 2 except that the column was not packed with immobilized acetate kinase or adenylate kinase and that no acetyl phosphate was added to the solution of starting material fed into the column.

The resulting reaction product was analyzed by the same method as used in Example 2; in addition to 2.0 mM (yield, ca. 40%) of $A_{p4}A$, 1.8 mM $A_{p3}A$, 1.5 mM AMP and 0.8 mM ADP were detected as by-products.

EXAMPLE 3

*Bacillus stearothermophilus* acetate kinase and adenylate kinase (commercially available from Seikagaku Kogyo Co., Ltd.), as well as the lysyl-tRNA synthetase prepared in Reference Example 2 and pyrophosphatase (manufactured by Böehringer Mannheim) were individually immobilized on CN-Br-activated Sepharose 4B (manufactured by Pharmacia Fine Chemicals). The thus immobilized enzymes (acetate kinase, 250 units; adenylate kinase, 350 units; lysyl-tRNA synthetase, 2 units; and pyrophosphatase, 20 units) were packed into a single column (capacity: 5 ml).

A starting material was prepared by dissolving 10 mM ATP, 5 mM acetyl phosphate and 50 mM lysine in 100 mM Hepes buffer (pH, 6.5) containing 10 mM magnesium chloride. This starting material was fed into the immobilized enzyme-packed column from the top at a flow rate of 1 ml/hr, with the reaction product being continuously withdrawn from the bottom of the column.

The resulting reaction product was analyzed by the same method as used in Example 1; 4.2 mM (yield: ca. 84%) of $A_{p4}A$ had formed but no $A_{p3}A$, AMP or ADP was detected. Consistent production of $A_{p4}A$ lasted for the next 15 hours.

COMPARATIVE EXAMPLE 3

Reaction was carried out as in Example 3 except that the column was not packed with immobilized acetate kinase or adenylate kinase and that no acetyl phosphate was added to the solution of starting material fed into the column.

The resulting reaction product was analyzed by the same method as used in Example 3: in addition to 1.8 mM (yield: ca. 36%) of $A_{p4}A$, 1.8 mM $A_{p3}A$, 1.6 mM AMP and 1.1 mM ADP were detected as by-products.

EXAMPLE 4

*Bacillus stearothermophilus* acetate kinase (commercially available from Seikagaku Kogyo Co., Ltd.), as well as the lysyl-tRNA synthetase prepared in Reference Example 2 and pyrophosphatase (manufactured by Böehringer Mannheim) were individually immobilized on CN-Br-activated Sepharose 4B (manufactured by Pharmacia Fine Chemicals). The thus immobilized enzymes (acetate kinase, 250 units; lysyl-tRNA synthetase, 2 units; pyrophosphatase, 20 units) were packed into a single column (capacity: 5 ml).

A starting material was prepared by dissolving 10 mM ATP, 5 mM acetyl phosphate and 50 µM lysine in 100 mM Hepes buffer (pH, 6.5) containing 10 mM magnesium chloride. This starting material was fed into the immobilized enzyme-packed column from the top at a flow rate of 1 ml/hr, with the reaction product being continuously withdrawn from the bottom of the column.

The resulting reaction product was analyzed by the same method as used in Example 1; in addition to 3.7 mM (yield: ca. 74%) of $A_{p4}A$, AMP had formed in an amount of 1.5 mM, but none of the $A_{p3}A$ and ADP that formed as by-products in Comparative Example 3 were detected. This results shows that the formation of undesired by-products can be effectively suppressed by using acetate kinase alone (i.e., without using adenylate kinase).

EXAMPLE 5

*Bacillus stearothermophilus* acetate kinase and adenylate kinase (commercially available form Seikagaku Kogyo Co,. Ltd.), as well as the leucyl-tRNA synthetase prepared in Reference Example 1 and pyrophosphatase (manufactured by Böehringer Mannheim) were individually immobilized on CN-Br-activated Sepharose 4B (manufactured by Pharmacia Fine Chemicals). The thus immobilized enzymes (acetate kinase, 300 units; adenylate kinase, 400 units; leucyl-tRNA synthetase, 10 units; and pyrophosphatase, 20 units) were packed into a single column (capacity: 5 ml).

A batch of starting material was prepared by dissolving 10 mM N6-carboxyethyl ATP, 5 mM acetyl phosphate and 10 pM leucine in 100 mM Hepes buffer (pH, 7.0) containing 10 mM magnesium chloride. This starting material was fed into the immobilized enzyme-packed column from the top at a flow rate of 1 ml/hr, with the reaction product being continuously withdrawn from the bottom of the column.

The resulting reaction product was analyzed by the same method as used in Example 1; $N^6$,$^6$-dicarboxyethyl adenosine tetraphosphate had formed in an amount of 2.6 mM (yield: ca. 52%).

COMPARATIVE EXAMPLE 4

Reaction was carried out as in Example 5 except that the column was not packed with immobilized acetate kinase or adenylate kinase and that no acetyl phosphate was added to the solution of starting material fed into the column.

The resulting reaction product was analyzed by the same method as used in Example 5; in addition to 1.2 mM (yield: ca. 24%) of $N^6$,$N^6$-dicarboxyethyl adenosine tetraphosphate, $N^6$-carboxyethyl adenosine triphosphate, $N^6$carboxyethyl AMP and $N^6$-carboxyethyl ADP were detected in amounts of 1.0 mM, 0.7 mM, and 0.8 mM, respectively.

While the invention has been described in detail and with reference to specific embodiments thereof, it will be apparent to one skilled in the art that various changes and modifications can be made therein without departing from the spirit and scope thereof.

What is claimed is:

1. A process for producing diadenosine tetraphosphate or a derivative thereof substantially without formation of adenosine triphosphate or derivatives thereof by reacting adenosine-5-triphosphate or a derivative thereof with an an amino acid under the catalytic action of aminoacyl-tRNA synthetase, wherein said reaction is carried out in the presence of an enzyme that convert adenosine-5'-monophosphate to adenosine-5'-diphosphate and an enzyme that converts adenosine-5'diposphate to adenosine-5'-triphosphate.

2. A process according to claim 1, wherein said aminoacyl-tRNA synthetase is produced from a microorganism having an optimum growth temperature of from 50° to 85° C.

3. A process according to claim 1, wherein said enzyme that converts adenosine-5'-diphosphate to adenosine-5'-triphosphate is acetate kinase.

4. A process according to claim 1, wherein said enzyme that converts adenosine-5'-diphosphate to adenosine-5'-triphosphate is produced from a microorganism having an optimum growth temperature of from 50° to 85° C.

5. A process according to claim 1, wherein said microorganism is selected from the group consisting of microorganisms of the genus *Bacillus;* microorganisms of the genus *Clostridium;* microorganisms of the genus *Thermoactinomyces;* microorganisms of the genus *Achromobacter;* microorganisms of the genus *Streptomyces;* microorganisms of the genus *Micropolyspora;* microorganisms of the genus Thermus; microorganisms of the genus *Thermomicrobium;* and microorganisms of the genus *Cardelia.*

6. A process according to claim 5, wherein said microorganism is selected from *Bacillus stearothermophilus, Bacillus brevis, Bacillus Coaqulans, Bacillus thrhmoproteolyticus* and *Bacillus acidocaldarius.*

7. A process according to claim 5, wherein said microorganism is selected from *Thermus aquaticus, Thermus thermophilus* and *Thermus flavus.*

8. A process according to claim 1, wherein said microorganism is *Bacillus stearothermophilus.*

9. A process according to claim 1, wherein said process is a batch process wherein said adenoine-5'-triphosphate or derivative thereof is added in an amount of at least 10 μM, and said amino acid is used in an amount at least 1 μM, and acetyl phosphate is added in an amount of from 10 to $1/10^2$ equivalents with respect to the concentration of adenosine-5'-triphosphate or derivative thereof.

10. A process according to claim 1, wherein said process is a batch process, wherein said adenosine-5'-triphosphate or derivative thereof is added in an amount of at least 1 mM, and said amino acid is used in an amount of at least 10 μM, and acetyl phosphate is added in an amount of from 2 to 1/10 equivalents with respect to the concentration of adenosine-5'-triphosphate or derivative thereof.

* * * * *